United States Patent
Buck (10) Patent No.: US 7,654,960 B2
(45) Date of Patent: Feb. 2, 2010

(54) METHOD AND DEVICE FOR ULTRASOUND MEASUREMENT OF BLOOD FLOW

(75) Inventor: Thomas Buck, Mettmann (DE)

(73) Assignee: Universität Duisburg-Essen, Essen (DE)

( * ) Notice: Subject to any disclaimer, the term of this patent is extended or adjusted under 35 U.S.C. 154(b) by 344 days.

(21) Appl. No.: 10/546,629

(22) PCT Filed: Feb. 26, 2004

(86) PCT No.: PCT/EP2004/001913

§ 371 (c)(1),
(2), (4) Date: Oct. 5, 2005

(87) PCT Pub. No.: WO2004/075754

PCT Pub. Date: Sep. 10, 2004

(65) Prior Publication Data

US 2006/0173347 A1    Aug. 3, 2006

(30) Foreign Application Priority Data

Feb. 27, 2003  (DE) ................ 103 08 821
Mar. 22, 2003  (DE) ................ 103 12 883

(51) Int. Cl.
 *A61B 8/00*   (2006.01)
(52) U.S. Cl. .............. 600/453; 600/450; 600/462; 600/465
(58) Field of Classification Search ........... 600/453, 600/454, 456, 450, 462, 465
See application file for complete search history.

(56) References Cited

U.S. PATENT DOCUMENTS

| 4,519,260 A | 5/1985 | Fu et al. ............ 73/861.25 |
| 4,873,985 A * | 10/1989 | Nakajima ............ 600/455 |
| 6,293,914 B1 | 9/2001 | Sumanaweera et al. ..... 600/465 |
| 6,423,006 B1 | 7/2002 | Banjanin ............ 600/453 |
| 6,464,642 B1 | 10/2002 | Kawagishi ............ 600/454 |

(Continued)

FOREIGN PATENT DOCUMENTS

EP       0 421 465 A2    4/1991

(Continued)

OTHER PUBLICATIONS

Buck, Thomas, et al., "Flow Quantification in Valvular Heart Disease Based on the Integral of Backscattered Acoustic Power Using Doppler Ultrasound", Proceedings of the IEEE, vol. 88, No. 3, Mar. 2000.

(Continued)

*Primary Examiner*—Eric F Winakur
*Assistant Examiner*—Katherine L Fernandez
(74) *Attorney, Agent, or Firm*—Woodard, Emhardt, Moriarty, McNett & Henry LLP (57) ABSTRACT

A method and a device (1) for ultrasound measurement of the blood flow through a heart valve are proposed. To permit a simple, automated measurement, it is proposed that the measurement area (9) of a measurement beam (7) is moved three-dimensionally by means of a multi-array transducer (11) and continuously evaluated for characteristic Doppler signals. It is further proposed to evaluate several measurement beams (7) with offset spatial, partially overlapping measurement areas (9) and/or several reference beams (8) with offset spatial measurement areas (10) for determination of the opening surface area, the volumetric flow rate, the flow volume and/or a value proportional thereto.

22 Claims, 7 Drawing Sheets

U.S. PATENT DOCUMENTS 6,544,181 B1 * 4/2003 Buck et al. ................... 600/455
6,773,399 B2 * 8/2004 Xi et al. ....................... 600/443
2003/0163046 A1 * 8/2003 Nohara et al. ............... 600/443

FOREIGN PATENT DOCUMENTS

WO     WO 00/51495 A1    9/2000

OTHER PUBLICATIONS

Buck, Thomas, et al., "The Power-Velocity Integral at the Vena Contracta A New Method for Direct Quantification of Regurgitant Volume Flow", Mass. Gen. Hospital, Harvard Medical School, Boston, Mass., Am. Heart Assoc., pp. 1053-1061, Mar. 29, 2000.

* cited by examiner

METHOD AND DEVICE FOR ULTRASOUND MEASUREMENT OF BLOOD FLOW

CROSS-REFERENCES TO RELATED APPLICATIONS

This application is a National Stage of International Application PCT/EP2004/975754 filed Feb. 26, 2004. Applicant claims foreign priority benefits under 35 U.S.C. 119(a)-(d) of the following foreign applications for patent: German Application No. 103 08 821.0, filed Feb. 27, 2003, and German Application No. 103 12 883.2, filed Mar. 22, 2003, all of which are hereby incorporated by reference in their entirety.

BACKGROUND OF THE INVENTION

The present invention relates to a method for ultrasound measurement and to a device for ultrasound measurement as disclosed herein.

In particular, the present invention relates to the ultrasound measurement of the blood flow in the human or animal body through a dynamic or irregular orifice, for example an insufficient or stenosed heart valve, a constricted vein or artery or similar. It is desirable, for example, to determine the cross-sectional surface area of flow, hereinafter shortened to (effective) opening surface area, the volumetric flow rate and/or the flow volume in a diseased heart valve, in particular the return flow through a diseased heart valve, in order thereby to be able to determine the severity of a valve defect and, if appropriate, perform a heart valve operation with optimum results.

WO 00/51495 A1, which forms the starting point of the present invention, discloses an ultrasound measurement method in which pulsed ultrasound signals are emitted and the backscattered ultrasound signals are evaluated on the basis of the Doppler technique.

For example, in the case of an insufficient heart valve, in order to determine the opening surface area, the volumetric flow rate, the flow volume and/or a value proportional thereto (hereinafter also shortened to measurement values) of the blood return flow, the measurement area of a reference beam must lie within the vena contracta (beam constriction) in the return flow of the blood through the heart valve, and the measurement area of a measurement beam must completely cover the vena contracta of the return flow through the insufficient heart valve. The positioning of the measurement areas has hitherto only been possible manually, and it requires great manual dexterity and considerable experience on the part of the operator. Moreover, a problem of the known method is that the orifice of an insufficient heart valve can be several centimetres at its maximum extent and for this reason the orifice can no longer be completely covered by the measurement area of a conventional measurement beam.

U.S. Pat. No. 6,464,642 B1 discloses a two-dimensional, so-called multi-array transducer for ultrasonic diagnostic in general, wherein a three-dimensional region of interest, e.g. the heart of a patient, can be displayed and Doppler signals evaluated.

In the present invention, a spatial area/volume is sonified, i.e. exposed to ultrasound, by a transmit beam. The backscatter of different sample volumes of this sonified volume is detected and evaluated, wherein the sample volumes are located at least essentially in a common plane and have different cross sections transversal to beam direction, but at least essentially the same extension in beam direction. In the present invention, the term "measurement area" designates the sample volume with the respective cross section transversal to beam direction. The backscattered ultrasound waves are called "measurement beam" and "reference beam", wherein the measurement beam has a greater measurement area than the reference beam. Preferably, the measurement area of the reference beam lies within the measurement area of the measurement beam. Thus, the terms "measurement beam" and "reference beam" designate in particular Doppler signals backscattered from the respective measurement area.

The object of the present invention is to provide a method and a device for ultrasound measurement of at least one of the opening surface area of a dynamic or irregular orifice through which a fluid flows, in particular blood, of the volumetric flow rate, and of flow volume through the orifice, permitting simple and preferably automated operation and/or an accurate measurement, in particular on a relatively large or irregularly shaped or dynamic orifice.

The above object is achieved by a method according to claim 1 or 13 or a device according to claim 21. Advantageous embodiments are subject of the subclaims.

According to one aspect of the present invention, the measurement area of the measurement beam, particularly within the heart, is moved three-dimensionally beforehand in a search mode, in particular by means of a suitably controlled matrix array transducer, while Doppler signals are continuously detected and are evaluated in respect of the occurrence of a Doppler spectrum characteristic of a vena contracta. For example, the measurement area is moved in a meandering configuration and in different planes in succession, in order to locate a spatial region in which there is a vena contracta of the fluid flowing through an orifice.

This greatly facilitates the practical application of the measurement method and the operation of a measurement device. In particular, automated detection of a vena contracta is possible without the operator requiring great experience or manual dexterity.

According to a further aspect of the present invention, and one which can also be realized independently, several measurement beams with offset spatial, partially overlapping measurement areas covering the orifice completely, and/or several reference beams with offset spatial measurement areas are evaluated for determination of the measurement values. This leads to several advantages.

The detection and evaluation of several offset measurement areas (these can optionally be the measurement areas of several measurement beams and/or of several reference beams) permit fine adjustment and, if appropriate, correction of motion or location during the measurement, so that it is possible to achieve a reliable complete coverage of the orifice by the measurement beams and/or a reliable positioning of a measurement area of a reference beam in the inside of the vena contracta of the fluid flowing through the orifice.

The mutually overlapping measurement areas of the measurement beams permit a reliable coverage of larger orifices too, so that improved and more accurate determination of the measurement values is made possible.

In particular, it is proposed to use what is called a matrix array transducer to generate preferably only one transmit beam to sonify a broad volume and to detect, preferably simultaneously if possible or sequentially, the measurement beams of different broad measurement areas and preferably the reference beams of different narrow measurement areas. This permits a simple, versatile structure, in which the directions of the beams and the depth range evaluated, and consequently the position of the measurement areas, can be controlled, in particular moved and adapted, electronically.

BRIEF SUMMARY OF THE INVENTION

A method for ultrasound measurement of at least one of an opening surface area of an orifice through which a fluid flows according to one embodiment of the present invention includes the step of evaluation of the back scatter of a measurement beam having a spatial measurement area and of a reference beam having a spatial measurement area. In terms of the disclosed method, the fluid is typically blood and the measurements include the volumetric flow rate and the flow volume through the orifice. The method is further defined by the characteristic that the spatial measurement area of the reference beam lies within the spatial measurement area of the measurement beam. Further, the method is characterized by several measurement beams with offset spatial, partially overlapping measurement areas covering the orifice completely. Further, reference beams with offset spatial measurement areas are evaluated for determination of at least one of the opening surface area, the volumetric flow rate, the flow volume, and any value proportional thereto.

Further advantages, features, properties and aspects of the present invention will become evident from the following description of a preferred illustrative embodiment with reference to the drawings.

DETAILED DESCRIPTION OF THE INVENTION

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
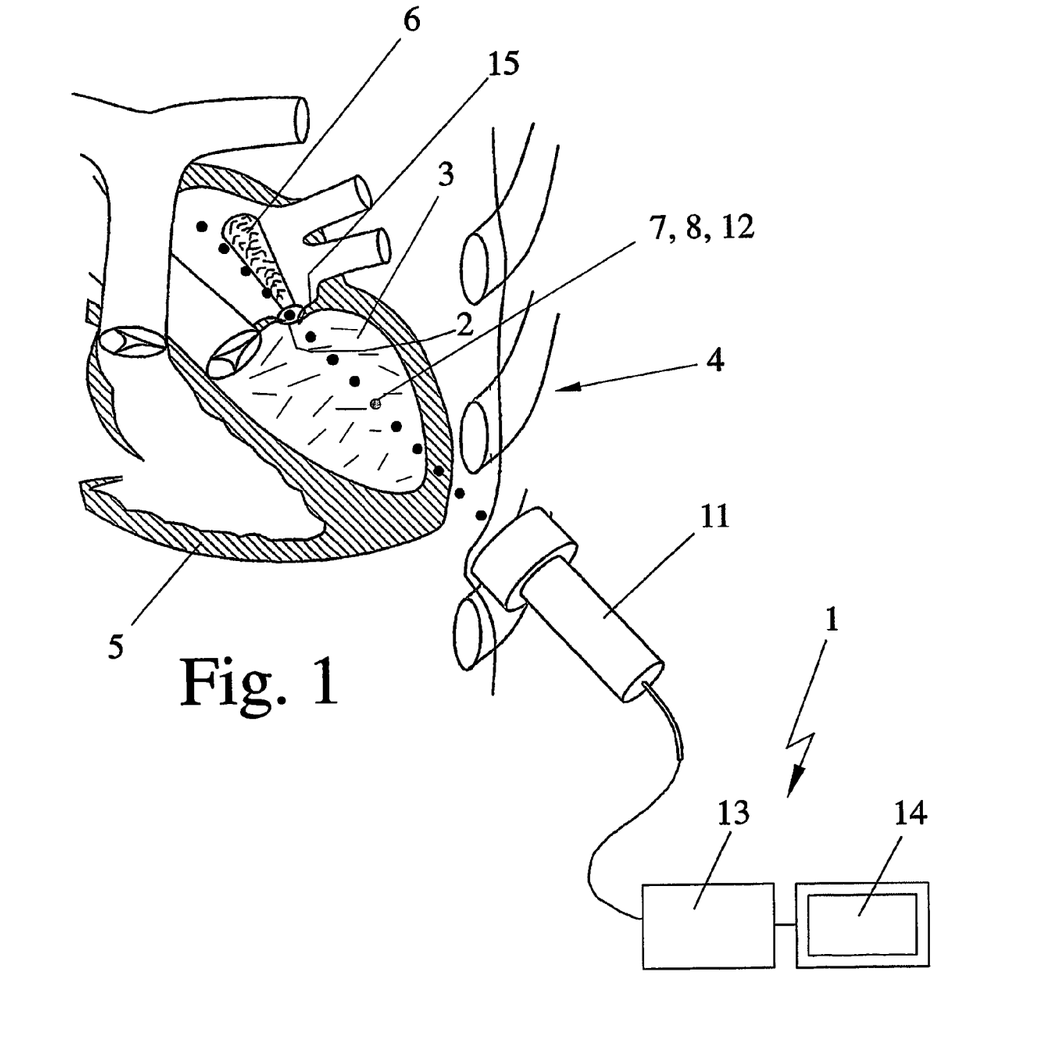
FIG. 1 shows a diagrammatic illustration of a proposed device for ultrasound measurement of the return flow through an insufficient heart valve.

The diagrammatic illustration in FIG. 1 shows a proposed device 1 and a proposed method for ultrasound measurement of the opening surface area of a dynamic and/or irregular orifice 2 through which a fluid flows, in particular blood 3, and/or of the volumetric flow rate and/or flow volume through the orifice 2.

In the diagrammatic illustration in FIG. 1, only part of a body 4 is indicated, with a heart 5 which is to be examined and through which blood 3 flows. A heart valve, in this case the mitral valve 15, is insufficient and therefore does not close completely during the contraction of the ventricles (hereinafter called systole), but instead forms the orifice 2 indicated diagrammatically in FIG. 1. During the systole, blood 3 flows back through the orifice 2.

By means of the proposed device 1 and the proposed method, it is possible to determine "measurement values", namely the effective opening surface area (for example a mean value, or the profile varying during the measurement or flow period) of the orifice 2, the volumetric flow rate of blood 3, in particular of the returning blood 3, which varies over time during the measurement or flow period, the total flow volume of the (returning) blood 3, and/or a proportional value.

However, the proposed method is not limited to determining the measurement values in a mitral valve, and instead can be used to determine the measurement values in any heart valve or in any other dynamic and/or irregular orifice 2, particularly one through which blood 3 flows, for example a hole in the cardiac septum, a stenosed vein or artery, or similar. Moreover, the proposed method is not limited to determining the measurement values in a single orifice 2, and instead can also determine the measurement values of several orifices 2 in succession (for example during systole in an insufficient mitral valve and during diastole (relaxation and filling of the ventricles) in an insufficient aortic valve) or simultaneously (for example in the case of two orifices 2 in an insufficient mitral valve or in an insufficient mitral valve and a stenosed aortic valve).

Figure 2:
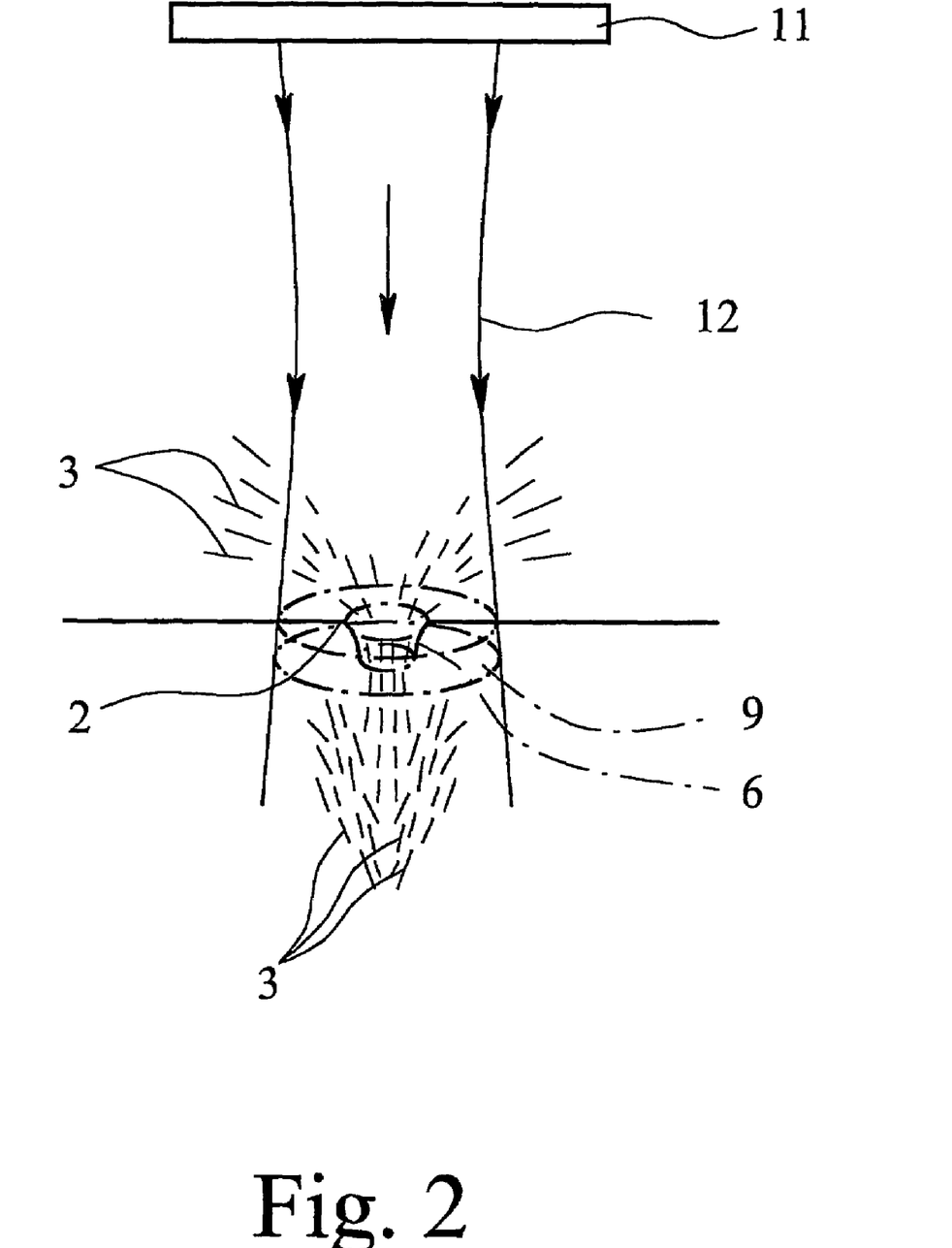
FIG. 2 shows a diagrammatic illustration of a transmit beam in ultrasound measurement of a vena contracta in an orifice.
Figure 3:
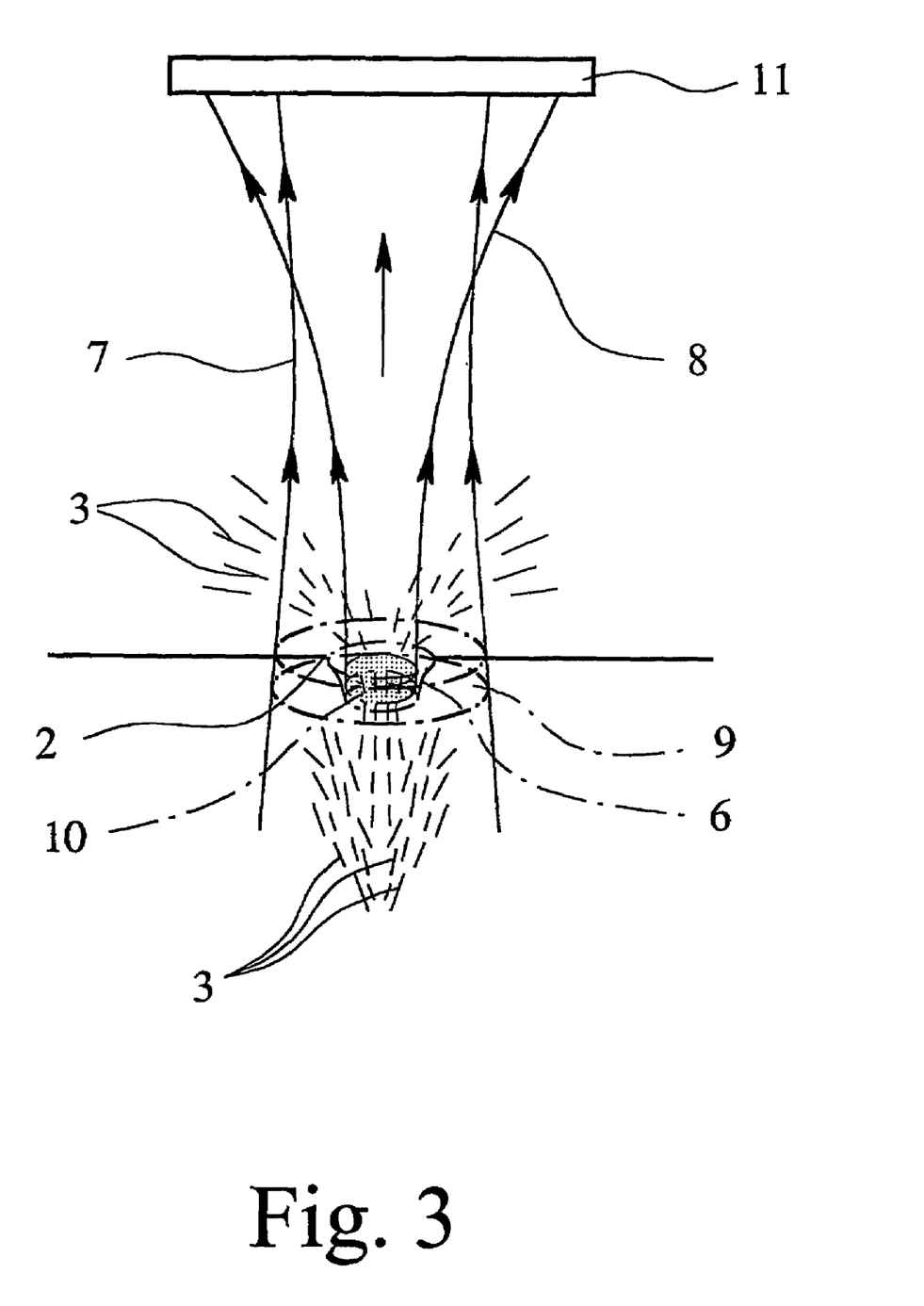
FIG. 3 shows a diagrammatic illustration of a measurement beam and of a reference beam in ultrasound measurement of a vena contracta in the orifice.

FIGS. 2 and 3 illustrate the basic principle of ultrasound measurement. A fluid, such as blood 3, flows through the diagrammatically indicated orifice 2, and forms adjacent to the orifice 2 in a region 6 a flow constriction with at least substantially laminar flow that is therefore also designated as vena contracta. Depending on several factors, as the shape of the orifice 2 and the blood 3, this laminar flow region 6 further narrows and merges increasingly into a turbulent current, as indicated diagrammatically in FIGS. 2 and 3.

In particular, the proposed method relates to locating and/or measuring a vena contracta with a flow constriction of factor 0.65 to 0.85 (surface area or diameter of the narrowed area 6 to surface area or diameter of the orifice 2).

Pulsed ultrasound signals are emitted in an ultrasound beam (transmit beam), as is indicated in FIG. 2, and the backscatter of ultrasound Doppler signals of a measurement beam 7 and of a reference beam 8 for determination of the measurement values is detected and evaluated, as is indicated in FIG. 3. The measurement beam 7 has a larger or wider measurement area 9. By contrast, the reference beam 8 has a smaller or narrower measurement area 10, which preferably lies centrally within the measurement area 9.

To generate and to receive or detect the ultrasound waves, a multi-array transducer 11 is preferably used. The transducer 11 has a multiplicity of ultrasound generators, for example piezo elements, which are arranged in particular in a matrix formation and whose phase and amplitude can be controlled in such a way that the ultrasound waves are emitted as transmit beam 12, as indicated in FIG. 2, and the direction of the transmit beam 12 and its width or cross section can be controlled electronically.

Accordingly, a spatial area/volume is sonified by the transmit beam 12. The measurement areas 9, 10 relate to different sample volumes of this sonified volume that are located at least essentially in a common plane and have different cross sections transversal to beam direction and that backscatter the measurement beam 7 and the reference beam 8, respectively.

As regards the transducer 11 and the behaviour of the ultrasound waves, it should be noted that ultrasound generation across a large surface area (aperture) on the transducer 11 results in a converging transmit beam 12, that is to say a transmit beam which is relatively narrow or thin in the target area. By contrast, a relatively wide transmit beam 12, that is to say a transmit beam 12 which is of greater cross section or less convergent, shown diverging in FIG. 2 for illustration, is obtained when the ultrasound waves are emitted only from a small transducer area or aperture, that is to say when ultrasound waves are emitted by only a relatively small number of ultrasound generators, for example those lying at the centre of the transducer 11.

The ultrasound waves also show the aforementioned behaviour when received. The size of the measurement area 9, 10 can be controlled by suitable choice of the receiving transducer aperture or area and evaluation. FIG. 3 shows that, with a small receiving transducer aperture or area, that is to say activation and evaluation of only some of the ultrasound generators/ultrasound receivers or piezo elements of the transducer 11, the received measurement beam 7 has a relatively wide measurement area 9, i.e. of large cross section. Conversely, the reference beam 8 has a narrow measurement area 10, i.e. of small cross section, with a large receiving transducer aperture or area, that is to say activation of many or all of the ultrasound generators/ultrasound receivers or piezo elements of the transducer 11.

The transducer 11 generates the transmit beam 12 and receives the measurement beam 7 and the reference beam 8 in brief succession and iteratively one after another, and in this connection it is preferable for only a wide transmit beam 12 to be generated which insonates both measurement areas 9 and 10 at the same time, so that the measurement beam 7 and the reference beam 8 can be detected and evaluated simultaneously, with on the one hand only a small receiving transducer aperture of the transducer 11 being evaluated and on the other hand a large receiving transducer aperture of the transducer 11 being evaluated, this preferably being done by parallel data processing at sufficient speed and simultaneously.

In particular, through the emission of pulsed ultrasound signals and the Doppler effect, it is possible to determine and fix the position and depth of the measurement areas 9, 10.

Therefore, by means of the multi-array transducer 11 preferably provided, or by means of any other suitable sound generator and receiver, both the spatial position and also the size (in particular the cross section and depth) of the measurement areas 9, 10 can be controlled or fixed by appropriate evaluation in the proposed ultrasound measurement method.

To perform the ultrasound measurements and to control the transducer 11, the device 1 preferably comprises, in addition to the transducer 11 itself, a control unit 13 and an associated display unit 14, as indicated in FIG. 1.

The power and velocity spectra of the Doppler signals and of the measurement beam 7 and reference beam 8 are detected and evaluated in particular.

Figure 4:
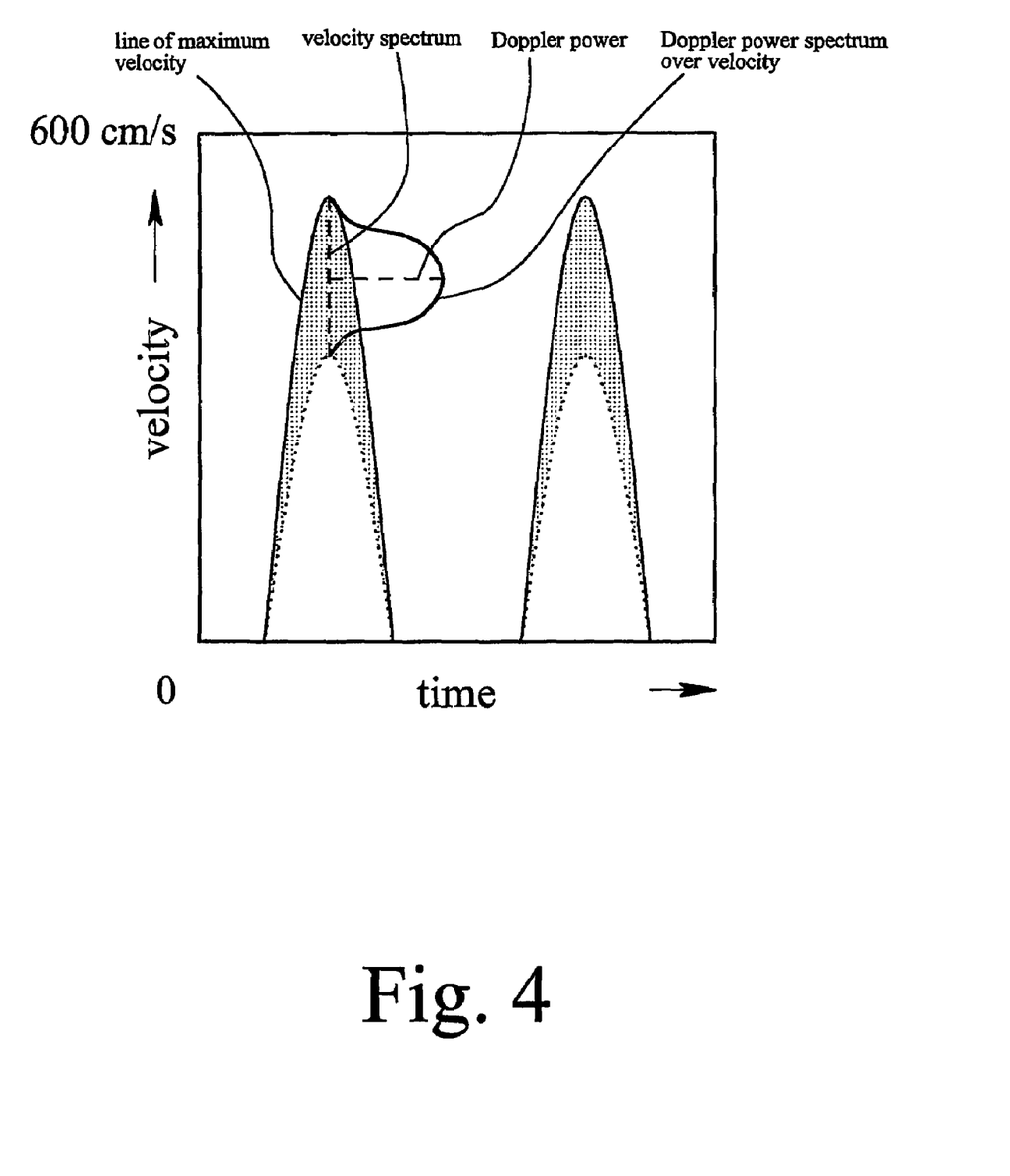
FIG. 4 shows a Doppler spectrum of a vena contracta.

FIG. 4 shows by way of example a diagrammatic Doppler spectrum (velocity as a function of time) of a vena contracta in a mitral valve, i.e. the return flow of blood 3 during two consecutive systoles. The Doppler spectrum does not in fact show a sharply contoured curve, but instead, per time, a spectrum of Doppler signals with different velocities and a spectrum of different backscattering power which varies with the partial measurement areas of different velocity, as is indicated by the dotted area in FIG. 4.

The integral of the power values over velocity or the velocity spectrum at a given time represents a measure of the opening surface area of the orifice 2 if the measurement area 9 completely encloses or covers the orifice 2. The reference beam 8 is chosen so that its measurement area 10 lies completely within the vena contracta, wherein the area (cross section) of the measurement area 10 is known or can be calculated.

By means of the reference beam 8, it is then possible, by suitable integral formation, to determine a calibration coefficient of the power backscattered from measurement area 10. This calibration coefficient, the known area (cross section) of the measurement area 10, and the power integral value obtained from the measurement beam 7 are used to determine the absolute value of the effective opening surface area of the orifice 2.

The effective opening surface area is the cross sectional area of flow actually acting in the vena contracts and is smaller by the factor 0.65-0.85 than the geometric opening surface area. The effective opening surface area is simply called "opening surface area" hereinafter and in the claims.

Accordingly, by integration of the product of power and velocity over the velocity or the velocity spectrum, it is possible to determine the absolute volumetric flow rate and, with additional integration over time, the absolute flow volume.

Thus, the measurement values can be obtained. Further details, in particular concerning the aforementioned measurement and determination of the measurement values or other aspects of the measurement, are set out in WO 00/51495 A1, which is herewith incorporated in its full scope as supplementary disclosure.

Figure 5:
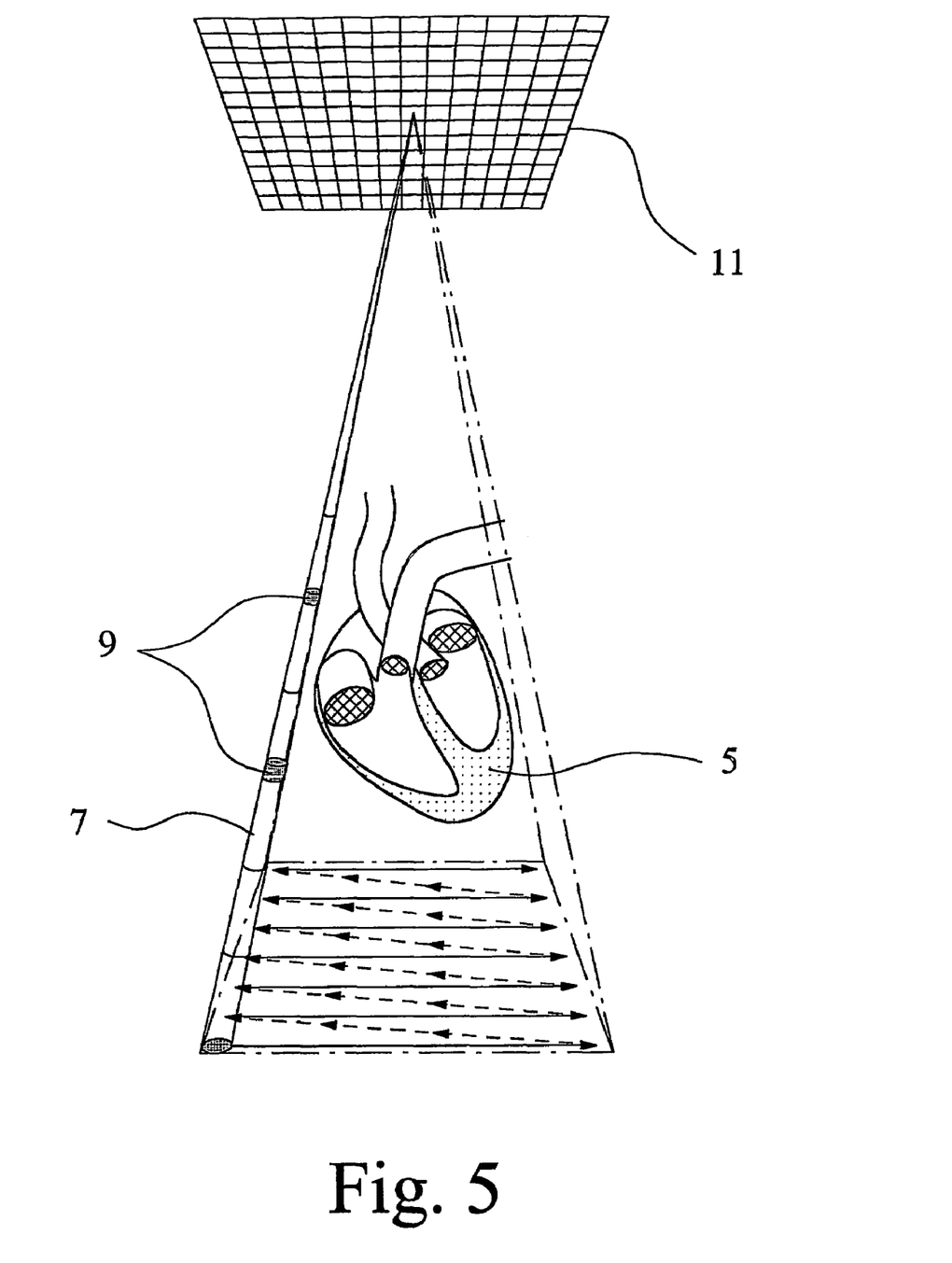
FIG. 5 shows a diagrammatic illustration of the device and method in a search mode.

FIG. 5 shows a diagrammatic illustration of the proposed device 1 and the proposed method in a search mode. Here, preferably only the wide transmit beam 12 and wide measurement beam 7 are used. The detection and evaluation of the reference beam 8 may, if necessary, be omitted in the search mode with a view to rapid processing.

The transmit beam 12 (not shown in FIG. 5) and the indicated measurement beam 7 are preferably moved in a meandering pattern, through corresponding control of the transducer 11, in order to scan or travel through the entire heart 5, e.g. as shown in FIG. 5 with broken lines in a pyramid shape, or through a partial volume of interest, e.g. one defined by an operator. Here, by means of suitable evaluation, the measurement area 9 of the measurement beam 7 is also positioned along the measurement beam 7 at different locations, so that, in view of the movement of the measurement beam 7, the measurement area 9 is moved in three dimensions, while Doppler signals are continuously detected and are evaluated in respect of the occurrence of a Doppler spectrum characteristic of a vena contracta.

The scanning or search process can take place quasi continuously or steplessly on account of the rapid data processing and short operating times. However, a large number of measurements are in fact carried out iteratively in succession, the position of the detected and evaluated measurement area 9 being changed in incremental stages in order to scan the whole of the possible or the intended volume for occurrence of a Doppler spectrum characteristic of a vena contracta. It also becomes clear that, from this systematic scanning a three-dimensional data set (volume) with the information of the spatial distribution of velocity and volume flow can be obtained and that this data set can be used later after the scanning has been completed to determine the occurrence of a vena contracta or even the measurement values of the vena contracta.

From what has been stated above, it will be clear that the proposed transducer 11 is preferably constructed in such a way that the ultrasound beams 7, 8, 12 can be moved in, for example, a conical spatial area with great spatial angle or cone angle. Accordingly, the transducer 11 is preferably what is called a two-dimensional matrix-array transducer, in other words an arrangement of ultrasound generators/ultrasound receivers or piezo elements which covers a large transducer aperture or area and extends in both area or aperture dimensions.

To determine whether there is a Doppler spectrum which is characteristic of a vena contracta, a filtering process is preferably carried out first. For example, all velocity values below a minimum limit $V_{MIN}$ of, for example, 100 cm/s are not taken into consideration and/or only velocity values are considered which show a bell-shaped or approximately normal-distribution velocity profile and/or lie above a minimum value of, for example, 20-50% of the maximum value of the respective spectrum. Thereafter, for the spectra or values preferably filtered or prepared in some other suitable way, a check is preferably made to ascertain

- whether the mean velocity exceeds a minimum value, or the mean velocity of a selected spectrum or measurement area 9 is maximal for all spectra and/or measurement areas 9,
- whether the width of the Doppler or velocity spectrum falls below a maximum value, or the width of a selected Doppler or velocity spectrum is minimal for all spectra and/or measurement areas 9,
- whether the power or the power integral over the velocity spectrum exceeds a minimum value, or the power or the power integral over a selected spectrum is maximal for all spectra and/or measurement areas 9,
- whether the Doppler spectrum shows an at least substantially continuous or constant line of maximal velocity, as is indicated in FIG. 4, and/or
- whether the velocity spectrum at a given time, in particular at maximum velocity, as is indicated in FIG. 4, shows at least substantially a Gaussian distribution or normal distribution.

It is only when at least one, two or preferably all of the aforementioned conditions are satisfied that the occurrence of a vena contracta is established or at least provisionally assumed, or displayed to an operator for selection, by the proposed method and proposed device 1, it being possible, if necessary, to switch to an imaging mode which depicts the spatial location of the suspected vena contracta.

After the occurrence of a vena contracta has been established, it is possible, either automatically or in response to a corresponding confirmation signal from an operator, to direct the measurement area 9, 10 of the measurement beam 7 and the reference beam 8 to the suspected vena contracta and then perform an ultrasound measurement to determine the measurement values, as already explained above or in particular as described in more detail below. The proposed device 1 and the proposed method thus permit automated navigation to, location, and measurement of a dynamic and/or irregular orifice 2 through which a fluid flows, such as blood 3, and/or of the volumetric flow rate and/or flow volume through the orifice 2.

Figure 6:
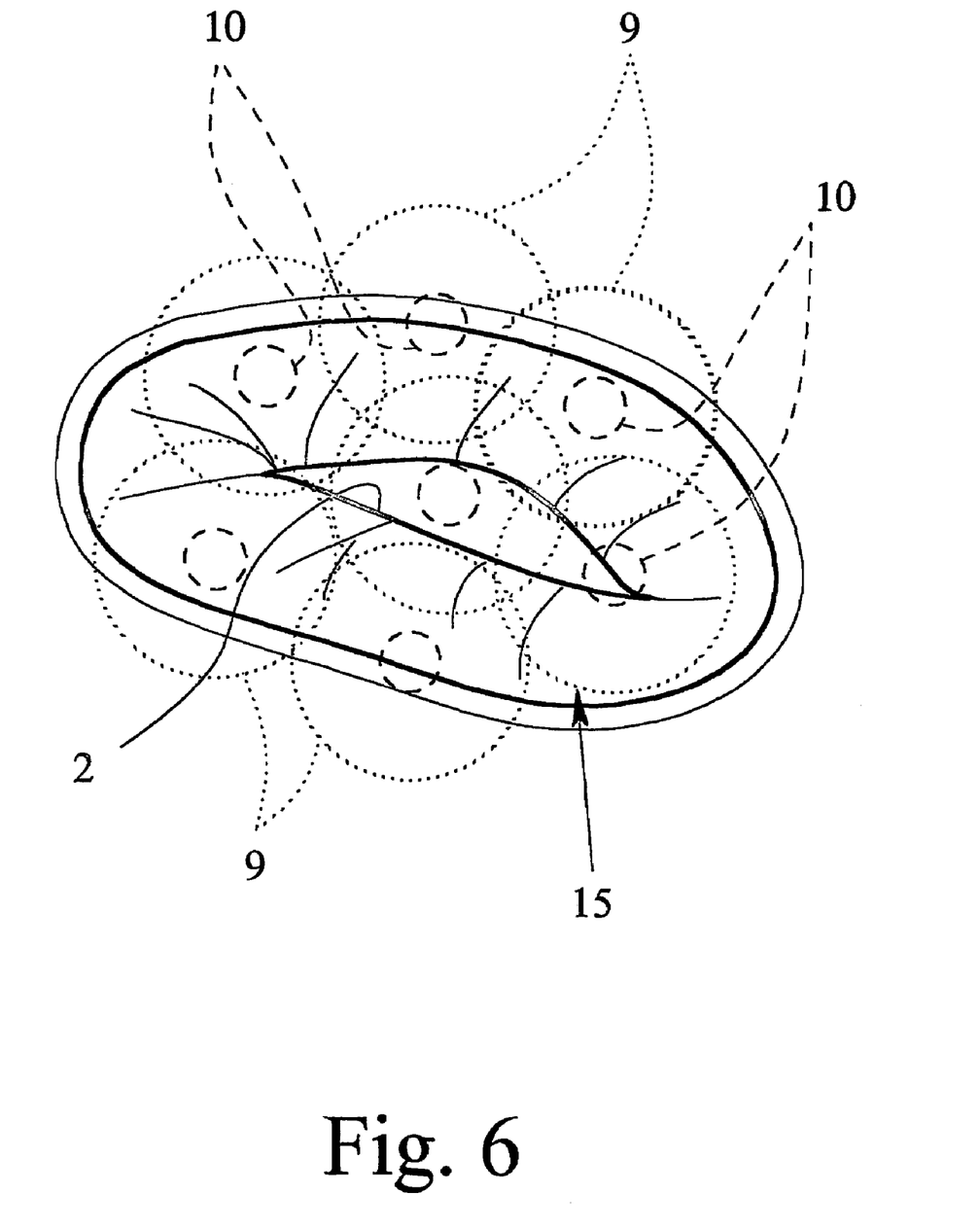
FIG. 6 shows a diagrammatic illustration of an insufficient heart valve and different positions of the measurement areas of the measurement beam and of reference beam in the ultrasound measurement.

A preferred approach in the actual measurement or determination of the measurement values is explained below with reference to FIG. 6. FIG. 6 shows a diagrammatic illustration of an insufficient heart valve, in particular a mitral valve which does not properly close during systole and accordingly presents the orifice 2. The orifice 2 can have a considerable size, in particular a length of several centimetres.

As indicated in FIG. 6, the maximum extent of the orifice 2 can be greater than the area that can be covered by the measurement area 9 of one measurement beam 7. In this connection, it should be borne in mind that the measurement area 9 cannot be arbitrarily enlarged, since the power or power density both of the transmit beam 12 and also of the measurement beam 7 decreases as the size or cross-sectional area increases; for an accurate measurement, however, a certain power or a certain signal-to-noise ratio is necessary in the signals that can be evaluated.

The proposed method and device 1 are preferably characterized by the fact that several measurement beams 7 with offset spatial, partially overlapping measurement areas 9 are detected and evaluated for determination of the measurement values. These measurement areas 9 are arranged, located and, if necessary, corrected to that the overlapping measurement areas 9 cover the orifice 2 completely, at least during the measurement.

In particular, a central measurement beam 7 with central measurement area 9 is surrounded, in a rosette formation, by the further measurement beams 7 with their measurement areas 9, as can be seen from the measurement areas 9 shown in FIG. 6. However, other configuration, e.g. two or more lines with offset measurement areas 9, can be provided, wherein the measurement areas 9 overlap in a similar manner.

Several measurement beams 7 with measurement areas 9, in particular all measurement beams 7 with measurement areas 9, are preferably detected and evaluated simultaneously or in succession iteratively within a measurement or measurement period. All measurement areas 9 are preferably evaluated cumulatively, it being possible for their overlaps areas 9 to be compensated, if necessary, so that it is possible to achieve a homogeneous power distribution which is as uniform as possible over the area formed by all the individual measurement areas 9.

The preferably peripheral superposition or any other suitable superposition of the measurement areas 9 has the result that the orifice 2 is covered completely by the measurement areas 9 and, accordingly, an accurate determination of the measurement values can be guaranteed.

Each measurement beam 7 is preferably assigned a reference beam 8, as indicated in FIG. 6 by the measurement areas 10 of reference beams 8 assigned to the measurement areas 9 of the measurement beams 7. In particular, the detection and evaluation for each measurement beam 7 and the reference beam 8 assigned to it take place simultaneously.

All the reference beams 8 are preferably detected and evaluated in succession iteratively within a measurement or measurement period.

The several offset measurement areas 9 of the measurement beams 7 permit fine adjustment and correction during the measurement period. If the power integral of the central measurement beam 7 or another measurement value no longer shows the highest value in relation to another measurement beam 7 with laterally offset measurement area 9, the measurement areas 9, 10 are corrected in such a way that the central measurement beam 7 with its measurement area 9 lies again in the centre of the orifice 2. This adjustment or correction is important in particular when the spatial position of orifice 2 is dynamic, that is to say changes during a measurement period, in particular moves laterally and/or when the position of the transducer 11 in relation to the vena contracta changes.

Alternatively or in addition, the aforementioned fine adjustment or correction can also be effected by evaluation of the values provided by the reference beams 8 or of values proportional thereto, the position of the central reference beam 8 with its measurement area 10 being continuously corrected particularly in such a way that the central measurement area 10, during the entire measurement period, preferably remains completely within the vena contracta.

To evaluate the reference beams 8, it should further be noted that a reference beam 8 is chosen to form a calibration coefficient for all the measurement beams 7, and in particular the highest calibration coefficient of all the reference beams 8 can be used as calibration coefficient for all the measurement beams 7.

The calibration coefficient of the reference beams 8 are preferably also continuously determined, and the position of the measurement areas 9, 10 is corrected, as a function of the calibration coefficient during a measurement period, particularly in such a way that the measurement areas 9, 10 are displaced in parallel into the direction from the central measurement area 9, 10 to where a higher calibration coefficient has occurred.

In the evaluation of the measurement beams 7 and reference beams 8 and determination of the measurement values, it is possible, if necessary, to ignore those backscatters or measurement beams 7 and reference beams 8 for which a correct position of the measurement areas 9, 10 was not present or not guaranteed, for example if the abovementioned criteria for the presence of a Doppler spectrum characterizing a vena contracta were not satisfied.

Figure 7:
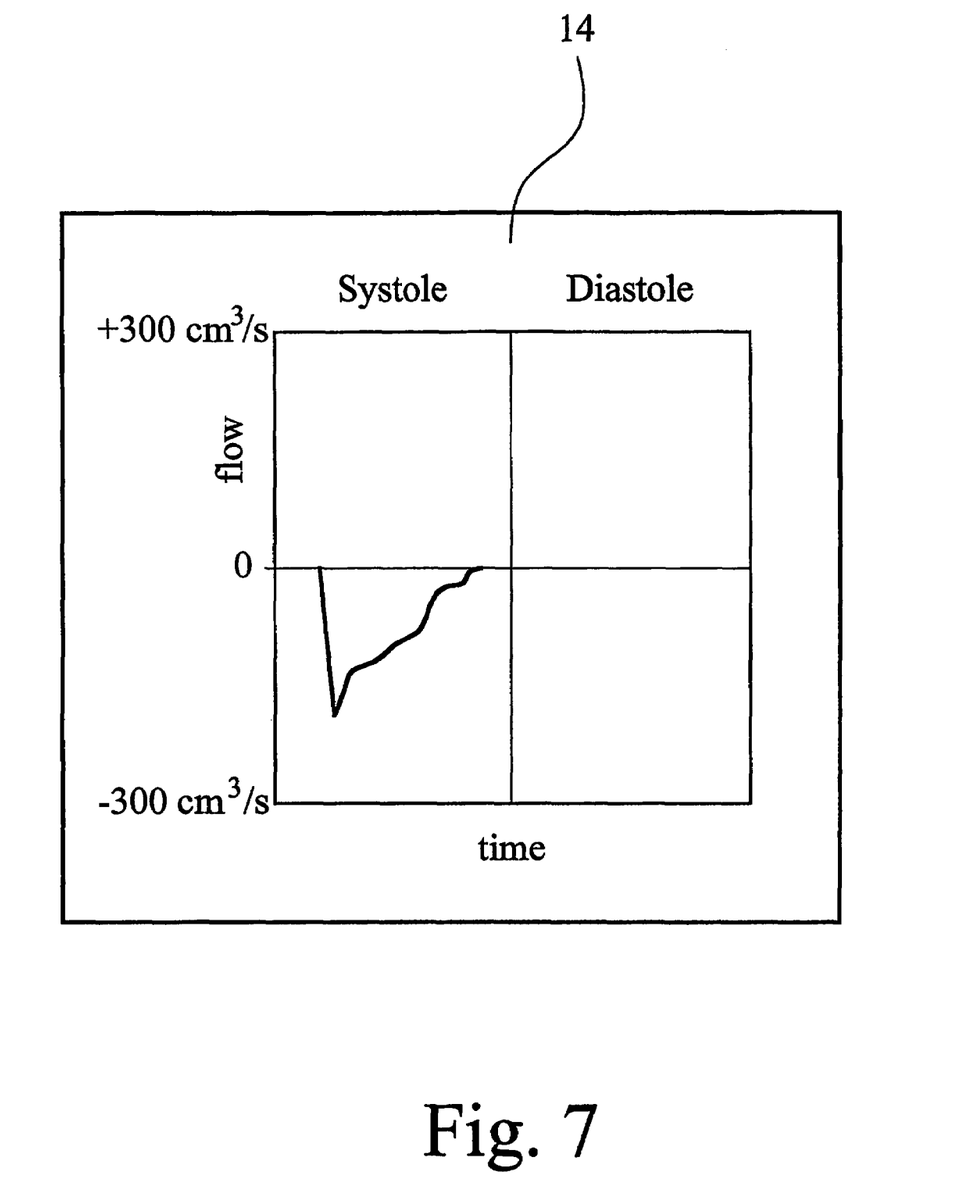
FIG. 7 shows a display unit of the device.

According to a further embodiment, the proposed method and the proposed device 1 are characterized by the fact that the measurement values for several separate orifices 2 can be determined either in succession or simultaneously during a measurement period. Thus, it is possible, for example, that two separate orifices 2, with in each case a Doppler spectrum characterizing a vena contracta, are detected in the search mode and are thereafter measured either in succession or simultaneously to determine the measurement values. The measurement values can then be displayed to the operator, for example by means of the display unit 14 shown diagrammatically in FIG. 7. Depending on the temporary status (systole or diastole) and the flow (positive or negative), it will be evident to the trained operator what type of heart valve and disease are involved, for example an insufficient mitral valve in the display shown, where positive speeds denote flow in the direction towards the transducer 11 and negative speeds denote flow in the direction away from the transducer 11.

The proposed device 1 and the proposed method are universally applicable, and the proposed automation in particular permits simple and safe operation and a rapid examination or measurement.

Preferably, the transducer 11 is not held manually by an operator, but fixed by means of a suitable support not shown or the like, in particular on the breast of a patient not shown.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A method for ultrasound measurement of at least one of an opening surface area of an orifice through which a fluid flows, the volumetric flow rate through the orifice and the flow volume through the orifice, comprising the steps of:

sonifying a region near an orifice through which bodily fluid is flowing by directing at least one transmit beam from an ultrasonic transducer toward said orifice;

sensing a plurality of measurement beams using said ultrasonic transducer, each one of said measurement beams having a respective measurement area, said measurement areas being offset spatially and partially overlapping, said measurement beams comprising Doppler signals backscattered from the respective measurement areas, said measurement areas collectively encompassing said orifice;

sensing at least one reference beam using said ultrasonic transducer, said at least one reference beam having a measurement area which is within said orifice, said reference beam comprising Doppler signals backscattered from the measurement area of said reference beam;

evaluating said at least one reference beam to determine a reference value, said reference value comprising a Doppler power calibration coefficient; and cumulatively evaluating the Doppler signals within said plurality of measurement beams in conjunction with said reference value to determine at least one of the opening surface area of the orifice, the volumetric flow rate through the orifice, the flow volume through the orifice, and any value proportional thereto;

wherein the Doppler signals of each measurement beam contribute to the overall value of said opening surface area, said volumetric flow rate, or said flow volume.

2. Method according to claim 1, wherein the orifice is at least one of dynamic and irregular.

3. Method according to claim 1, wherein a central measurement area of a measurement beam is surrounded in a rosette pattern by several measurement areas of further measurement beams.

4. Method according to claim 1, wherein, for each measurement beam, a reference beam is evaluated whose measurement area lies inside the measurement area of the associated measurement beam.

5. Method according to claim 1, wherein the several measurement beams are evaluated cumulatively, with overlaps of their measurement areas being compensated, in order to generate a power profile which is as homogeneous as possible across the entire area.

6. Method according to claim 1, wherein the measurement area of a central reference beam is surrounded in a rosette formation by several measurement areas of further reference beams.

7. Method according to claim 1, wherein the measurement area of a reference beam is directed into the inside of a vena contracta of the fluid flow through the orifice.

8. Method according to claim 1, wherein one reference beam forms a reference value for all the several measurement beams.

9. Method according to claim 1, wherein the reference values of several reference beams are continuously determined and the position of the measurement areas is corrected as a function of the reference values during a measurement period, so that the measurement area of a central reference beam remains within a vena contracta of the fluid flow through the orifice.

10. Method according to claim 1, wherein the reference values of several reference beams are continuously evaluated during a measurement period, and the measurement areas of the reference beams and of the measurement beams are shifted during a measurement period when the reference value of the central reference beam reaches or drops below a reference value of another reference beam into the direction from the central measurement area to the measurement area of the last-mentioned reference beam.

11. Method according to claim 1, wherein power spectra of Doppler signals of the backseattered measurement beams and the at least one reference beam are evaluated as backscatter to determine at least one of the opening surface area, the volumetric flow rate, the flow volume and the value proportional thereto.

12. Method according to claim 1, wherein pulsed ultrasound Doppler signals are used.

13. Method according to claim 1, wherein a transmit beam is generated by means of a matrix array transducer and directed to desired measurement areas.

14. Method according to claim 1, wherein the several measurement beams and the at least one reference beam are detected by means of a matrix array transducer as a function of the measurement areas.

15. Method according to claim 1, wherein during a measurement period, at least one of the opening surface area, the volumetric flow rate, the flow volume and the value proportional Thereto is determined separately for two or more separate orifices.

16. Method according to claim 1, wherein at least one of the opening surface area, the volumetric flow rate, the flow volume and the value proportional thereto is displayed.

17. Method according to claim 1, wherein the measurement area of at least one of the measurement beams is moved three-dimensionally beforehand in a search mode, while Doppler signals are continuously detected and evaluated in respect of the occurrence of a Doppler spectrum characteristic of a vena contracta, so tat thereafter for the determination, the measurement area of the reference beam is directed into the inside of the vena contracta of the fluid flow through the orifice and the measurement area of the measurement beam is directed into The area of the vena contracta of the fluid flow through the orifice.

18. Method according to claim 17, wherein, in order to detect a vena contracta, at least one of the following conditions are evaluated:
whether the mean speed of the flow determined by means of the Doppler signals exceeds a minimum value or is maximal;
whether the width of the speed spectrum of the flow determined by means of the Doppler signals falls below a maximum value;
whether the power or the power integral over the speed of the flow determined by means of the Doppler signals exceeds a minimum value or is maximal;
whether the Doppler spectrum shows an at least substantially continuous or constant line of maximal speed; and
whether the speed spectrum of the flow determined by means of the Doppler signals at a given time and at maximum speed shows at least one of a substantially Gaussian distribution or normal distribution.

19. Device for ultrasound measurement of at least one of an opening surface area of a dynamic or irregular orifice through which a fluid flows, in particular blood, of the volumetric flow rate and of the flow volume through the orifice, comprising:
a means for evaluation of the power spectrum of Doppler signals of a measurement beam having a spatial measurement area and of a reference beam having a spatial measurement area, wherein the spatial measurement area of the reference beam lies within the spatial measurement area of the measurement beam;
a matrix away transducer for generating a transmit beam and for detecting the measurement beam and the reference beam;
wherein the device is adapted such that several measurement beams with offset spatial, partially overlapping measurement areas covering the orifice completely and at least one of one measurement beam and of several reference beams with offset spatial measurement areas can be detected and evaluated for determination of at least one of the opening surface area, the volumetric flow rate, the flow volume and any value dependent thereon, and
wherein the Doppler signals of each measurement beam contribute to the overall value of said opening surface area, said volumetric flow rate, or said flow volume.

20. A method for ultrasound measurement of the opening surface area of a dynamic or irregular orifice through which a fluid flows, and/or the volumetric flow rate and/or flow volume through the orifice, comprising the steps of:
sonifying a region near an orifice through which bodily fluid is flowing by directing at least one transmit beam from an ultrasonic matrix array transducer toward said orifice;
sensing a measurement beam using said ultrasonic matrix array transducer, said at least one measurement beam having a first measurement area, said measurement beam comprising Doppler signals backscattered from said spatial measurement area, said measurement area being near said orifice;
automatically moving the measurement area of said measurement beam three-dimensionally in a search mode without moving said matrix array transducer, while said Doppler signals are continuously detected and evaluated, to determine the location of a vena contracta;
sensing at least one reference beam using said ultrasonic matrix array transducer, said at least one reference beam having a second measurement area which is within said vena contracta, said reference beam comprising Doppler signals backscattered from the second measurement area;
evaluating the reference beam to determine a reference value, said reference value comprising a Doppler power calibration coefficient; and
evaluating the Doppler signals within said measurement beam in conjunction with said reference value to determine at least one of the opening surface area of the orifice, the volumetric flow rate through the orifice, the flow volume through the orifice, and any value proportional thereto.

21. Method according to claim 20, wherein, in order to detect the vena contracta, at Least one of the following conditions are evaluated:
whether the mean speed of the flow determine by means of the Doppler signals exceeds a minimum value or is maximal;
whether the width of the speed spectrum of the flow determine by means of the Doppler signals falls below a maximum value;
whether the power or the power integral over the speed of the flow determine by means of the Doppler signals exceeds a minimum value or is maximal;
whether the Doppler spectrum of the flow determine by means of the Doppler signals shows an at least substantially continuous or constant line of maximal speed; and
whether the speed spectrum at a given time and at maximum speed shows at least one of a substantially Gaussian distribution or normal distribution.

22. Method according to claim 20, wherein a three-dimensional data set with the information of the spatial distribution of velocity and volume flow is obtained in the search mode and stored so that this data set can be used later to determine at least one of the occurrence of a vena contracta, the opening surface area, the volumetric flow rate, the flow volume and a value dependent thereon.

* * * * *

UNITED STATES PATENT AND TRADEMARK OFFICE
CERTIFICATE OF CORRECTION

PATENT NO. : 7,654,960 B2  Page 1 of 1
APPLICATION NO. : 10/546629
DATED : February 2, 2010
INVENTOR(S) : Thomas Buck It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 673 days.

Signed and Sealed this

Twenty-eighth Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,654,960 B2 | Page 1 of 1 |
| APPLICATION NO. | : 10/546629 | |
| DATED | : February 2, 2010 | |
| INVENTOR(S) | : Buck | |

It is certified that error appears in the above-identified patent and that said Letters Patent is hereby corrected as shown below:

In column 10, line 63, in claim 11, please replace the word "backseattered" with --backscattered--.

In column 11, line 23, in claim 17, please replace the word "tat" with --that--.

In column 11, line 50, in claim 19, please remove ", in particular blood,".

In column 11, line 59, in claim 19, please replace the word "away" with --array--.

Signed and Sealed this
Third Day of May, 2011

David J. Kappos
*Director of the United States Patent and Trademark Office*